United States Patent [19]
Fischer et al.

[11] Patent Number: 5,877,627
[45] Date of Patent: Mar. 2, 1999

[54] DEVICE FOR DETECTING SECONDARY MAGNETIC FIELDS INDUCED IN AN ORGANISM BY PULSED MAGNETIC FIELDS

[75] Inventors: Gerhard Fischer, Vaduz, Liechtenstein; Ulrich Warnke, Scheidt, Germany

[73] Assignee: Dr. Fischer Aktiengesellschaft, Vaduz, Liechtenstein

[21] Appl. No.: 628,722

[22] PCT Filed: Oct. 8, 1994

[86] PCT No.: PCT/EP94/03325

§ 371 Date: Jun. 11, 1996

§ 102(e) Date: Jun. 11, 1996

[87] PCT Pub. No.: WO95/10228

PCT Pub. Date: Apr. 20, 1995

[30] Foreign Application Priority Data

Oct. 14, 1993 [DE] Germany .......................... 43 35 102.6

[51] Int. Cl.⁶ ............................. G01N 27/72; G01R 33/12
[52] U.S. Cl. ......................... 324/239; 600/14; 128/653.1
[58] Field of Search ................................. 324/239, 201, 324/244, 260, 307, 318, 322; 128/653.1, 653.2; 600/9–15

[56] References Cited

U.S. PATENT DOCUMENTS

| | | |
|---|---|---|
| 4,819,648 | 4/1989 | Ko ........................................... 324/236 |
| 4,969,469 | 11/1990 | Mills ........................................ 324/244 |
| 4,985,678 | 1/1991 | Gangarosa et al. ...................... 324/318 |
| 5,073,858 | 12/1991 | Mills ........................................ 324/201 |
| 5,152,288 | 10/1992 | Hoenig et al. ........................... 324/262 |
| 5,480,373 | 1/1996 | Fischer et al. ............................. 600/14 |

FOREIGN PATENT DOCUMENTS

| | | |
|---|---|---|
| 3445047 | 6/1986 | Germany . |
| 4221739 | 1/1993 | Germany . |
| 9114947 | 10/1991 | WIPO . |
| 9302618 | 2/1993 | WIPO . |

*Primary Examiner*—Sandra L. O'Shea
*Assistant Examiner*—Jay M. Patidar
*Attorney, Agent, or Firm*—Robert W. Becker & Associates

[57] ABSTRACT

A device for determining the effect of pulsed primary magnetic fields on an organism has a measuring pick-up for secondary magnetic field signals generated by the organism in response to the primary magnetic fields. An evaluation circuit for the secondary magnetic field signals is provided. The evaluation circuit has a first memory device with a memory unit. The evaluation circuit has a control device. The control device includes a device for processing sequential secondary magnetic field signals such that the sequential secondary magnetic field signals are combined to a cumulative signal in the memory unit. The cumulative signal is used as an output signal of the evaluation circuit.

30 Claims, 3 Drawing Sheets

DEVICE FOR DETECTING SECONDARY MAGNETIC FIELDS INDUCED IN AN ORGANISM BY PULSED MAGNETIC FIELDS

BACKGROUND OF THE INVENTION

The present invention concerns a device for determining the effect of pulsed magnetic fields on an organism.

Pulsating magnetic fields affecting an organism are, for example, of particular interest with regard to the transport of ions from intracorporeal fluids into and through the vessel walls and membranes of organisms which surround these fluids. Devices for this purpose have been described, for example, in German published document 42 21 739 A1. This laid open document also describes devices for determining the effect of such magnetic fields. For this purpose, the organism is either subjected to an approximately sinusoidal signal in the frequency range of 100 kHz during the pulse intervals, and the corresponding received signal is picked up by a measurement coil, or the measurement coil is used with a suppression circuit to pick up the secondary field signal which is induced in the measurement coil following each impulse in the primary magnetic field by means of the secondary and transient magnetic field arising within the organism.

The present invention concerns a further development of such a device, with the aim of increasing the amount of information conveyed by the measurement results.

SUMMARY OF THE INVENTION

The device for determining the effect of pulsed primary magnetic fields on an organism according to the present invention is primarily characterized by:
- a measuring pick-up for secondary magnetic field signals generated by the organism in response to the primary magnetic fields;
- an evaluation circuit for the secondary magnetic field signals;
- the evaluation circuit comprising a first memory device with a memory unit;
- the evaluation circuit further comprising a control device;
- the control device comprising a means for processing sequential secondary magnetic field signals such that the sequential secondary magnetic field signals are combined to a cumulative signal in the memory unit; and
- wherein the cumulative signal is used as an output signal of the evaluation circuit.

The measuring pick-up is preferably a measuring coil.

The evaluation circuit has a suppression circuit connected between the measuring pick-up and the memory unit, the suppression circuit comprising a control unit for allowing processing of the sequential secondary magnetic field signals only in a periods of rest after the primary magnetic pulses.

Preferably, the control device is designed such that the cumulative signal is a mean value of the sequential secondary magnetic field signals.

Expediently, the control device comprises a correlator for calculating the mean value, wherein the correlator performs an algebraic addition for the sequential secondary magnetic field signals and a geometric addition for disruptive signals.

The evaluation circuit, the memory unit and the control device are designed such that an amplitude of the sequential secondary magnetic field signals is determined.

Advantageously, the evaluation circuit, the memory unit and the control device are designed such that an energy contents of the sequential secondary magnetic field signals is determined.

The evaluation circuit, the memory unit and the control device are designed such that differential signals are calculated from the sequential secondary magnetic field signals and the differential signals are saved.

The device preferably further comprises a second memory device for saving the cumulative signals.

The evaluation circuit and the control device are designed such that, at the beginning of subjecting the organism with the pulsed primary magnetic fields, the cumulative signals are sent to the second memory device.

The evaluation circuit and the control device are designed such that, at the end of subjecting the organism with the pulsed primary magnetic fields, the cumulative signals are sent to the second memory device.

The evaluation circuit and the control device are designed such that, at the beginning and the end of subjecting the organism with the pulsed primary magnetic fields, the cumulative signals are sent to the second memory device.

The second memory device is preferably detachable from the device, and, in a preferred embodiment, is a chip card.

The second memory device comprises a plurality of sectors, wherein a first one of the sectors saves the cumulative signals as measured values, a second sector saves treatment parameters, and a third sector saves personal data of the organism.

The device may also further comprise a circuit for deriving a trigger signal from movements of the organism in order to ensure comparability of the sequential secondary magnetic field signals, wherein the evaluation circuit has a trigger element and wherein the trigger signal is sent to the trigger element so that the evaluation circuit is operational only at specific times determined by the trigger signal.

For ensuring comparability of the sequential secondary magnetic field signals, the measuring coil comprises means for securely attaching the measuring coil to the organism.

The device also further comprises an auxiliary coil for ensuring comparability of the sequential secondary magnetic field signals, wherein the second measuring coil is positioned remote from the measuring coil such that the auxiliary coil is exposed only to disruptive fields that also penetrate the measuring coil and wherein the measuring coil and the auxiliary coil are connected to an input of the evaluation circuit such that output signals of the measuring coil and the auxiliary coil are sent via an electric differential circuit to the input.

The measuring coil comprises a means for shielding against exterior magnetic disruptive fields in order to increase the signal-to-noise ratio of the evaluation circuit.

The device may further comprise an auxiliary chemical (electrochemical) gas measuring device for detecting gases emanating from the organism.

The device also may comprise a breathing mask, wherein the gas measuring device is integrated into the breathing mask.

The breathing mask comprises three connectors, wherein a first one of the connectors supplies compressed breathing air, a second one of the connectors receives the gas measuring device, and a third one of the connectors receives a controller for ensuring a substantially constant pressure for gas flow form a gas inlet of the measuring device to the exterior of the breathing mask.

The gas measuring device is a sensor for detecting at least one gas selected from the group consisting of HCl and NO.

The device preferably further comprises an auxiliary chemical (electrochemical) measuring device for detecting organism-specific fluids.

The device may also include a radiation thermometer for detecting the temperature of the organism, wherein the thermometer has an output and provides the measured temperature value as an electric signal at the output.

The radiation thermometer is designed to measure the temperature of the organism in one the bodily orifices. Preferably, the radiation thermometer measures the temperature of the organism in the ear of the organism.

The device may also include a device for applying the pulsed magnetic fields to the organism.

A blocking device for allowing activation of the device only when the second memory device is operational may be provided.

The device may also further comprise a blocking device for allowing activation of the device only during late morning hours and late afternoon hours.

In a device for determining the effect of pulsed primary magnetic fields on an organism, in which an evaluation circuit is provided for the signals derived from the organism by means of a measurement (measuring) pick-up designed, in a preferred embodiment, as a measurement (measuring) coil for secondary field signals (secondary magnetic field signals), this is achieved in accordance with the present invention due to the facts that the evaluation circuit has a storage (memory) device, that the storage device has a storage medium (memory unit) to which a control device is allocated, which is designed in such a way that several consecutive individual secondary magnetic field signals are written into the storage medium so that they are combined into a cumulative signal in the storage medium, and that this cumulative signal consisting of several individual signals is the output signal of the evaluation circuit.

There are several advantageous evaluation methods available for determining the effect. For example, it is possible to determine the amplitude value of secondary field signals and/or the energy content of secondary field signals in the evaluation circuit. An advantageous form of this design is to allocate to the evaluation circuit a circuit for determining the average (mean) value of several individual values. In a preferred embodiment, this allocated circuit takes the form of a correlator which performs algebraic addition on the individual values and geometric addition on the disruptive signals. In this manner, it is possible to raise the signal-to-noise ratio considerably, thereby increasing the accuracy of the information conveyed in the measurement results.

The embodiment in accordance with the present invention also makes it possible to create the evaluation circuit in such a manner that it feeds to the storage medium the value occurring at the beginning and/or the end of each occasion when the organism is subjected to pulsed magnetic fields. In accordance with a further advantageous embodiment, the evaluation circuit is designed so as to produce differential signals from the secondary field signals and store (save) them.

In an advantageous embodiment, the storage medium used is a memory device which can be separated from the device, and which may also be an additional storage medium (money device), in particular a memory chip card. It is also possible to divide the storage medium into several areas, one of which is used for storing measured values which have been determined, another of which is used for storing treatment data (parameters), and another is intended as a storage medium area with restricted access for storing personal data related to the organism.

The secondary magnetic fields are very weak, and so it is to be recommended that precautions be taken to ensure that the individual signals can be evaluated in a comparable manner in the storage medium. Such comparability is directly proportional, to the quality of the signal-to-noise ratio. An advantageous solution for this consists, for example, in having an auxiliary coil conelated with the measurement coil used for picking up the secondary signal from the organism, whereby this other coil is located away from the measurement coil so that it is only principally affected by the disruptive magnetic fields which also affect the measurement coil, and so that both coils are connected to the evaluation circuit input using an electrical differential circuit with respect to their output signals which are derived from the disruptive fields. For example, the other coil can be positioned at a certain distance above the measurement coil, so that it only principally picks up the spatial disruptive signals but to all intents and purposes does not pick up any secondary signal, whereas the measurement coil not only picks up the spatial disruptive signal, but also the secondary signal. Provided that the dimensions and number of windings of both coils are arranged so that they produce output signals which are at least approximately identical from the spatial interference, the coils can be linked together in an inverse electrical connection and connected to the evaluation circuit input. This results in a considerably improved signal being fed to the storage medium for further processing. It is also possible to harmonise the signals received from both coils with regard to the spatial interference using damping elements or control amplifiers, which, in a preferred embodiment, are adjustable. In order to improve the signal-to-noise ratio in the evaluation circuit, it is also possible to provide the measurement coil with a magnetic shield to protect it from external disruptive magnetic fields (magnetic spatial interference).

In this connection, means by which to remove the influence of changes in distance between the measurement pick-ups and the organism during the measurement process, in particular changes due to breathing movements, are advantageous. One possibility of doing so involves fixedly connecting the measurement pick-up to the organism. Another possibility which can be used additionally if need be consists of a circuit which derives a trigger signal in response to the movements of the organism, and to provide the evaluation circuit with a trigger element to which the trigger signal is sent, whereby the evaluation circuit is only operational at specific times as determined by the trigger signal, at which times the distance between the measurement pick-up, for example the measurement coil, and the relevant part of the organism is the same. This derivation circuit can take the form of, for example, a photoelectric barrier.

In a further embodiment of the present invention, and in particular as an additional feature, an electrochemical recording device or sensor is provided as a measurement pick-up for gases evolved by the organism or for liquids specific to the organism. In the case of a measurement pick-up (gas measuring device) for gases, this is incorporated to best advantage within a breathing mask. In a beneficial configuration, this measurement pick-up is a sensor device for hydrogen chloride (HCl) and/or nitrogen monoxide (NO).

In another further embodiment of the present invention, and in particular as an additional feature, a radiation thermometer is provided as a measurement pick-up for the temperature of the organism, whereby the radiation thermometer gives the temperature value as an electrical signal at its output. It has proven to be an advantage to produce the radiation thermometer as a measurement organ for measuring the temperature of the organism in one of its bodily openings, in particular in the ear of the organism. It is beneficial if the device is designed in such a way that it forms a single device unit together with a device for subjecting an organism to pulsating magnetic fields.

Furthermore, it is beneficial if a blocking device is provided in a device whose evaluation circuit is connected to an additional storage medium, in particular a removable storage medium, whereby the blocking device only permits activation of the device when the additional storage medium is switched on.

It has proven to be advantageous if a blocking device is provided in the device which only permits the device to be activated during the late morning and/or late afternoon.

A device and a process of prior art for measuring weak magnetic fields which are dependent on location and time is familiar from U.S. Pat. No. 5,152,288, in which a number of measurement pick-ups, there referred to as "superconducting quantum interference devices (SQUIDS)" pick-up the weak magnetic fields given off by the organism to be studied. Amongst other objects, SQUIDS are described with respect to their design, method of operation and application in a book entitled "Mikroelektronische Sensoren" by Waldmann and Ahlers, VEB Verlag Technik/Berlin, 1st edition 1989, pages 148/149, with bibliographical references. As shown in FIG. 7 of the printed patent specification referred to above, the signals picked up using SQUIDS are fed to, amongst other things, a storage medium, from where the stored values can be used further to derive an anatomical image of the object under investigation or to derive a model of the object under investigation. In accordance with this description, and as demonstrated by further descriptions in the printed patent specification, this is a device for tomography and is not a device for determining the effect of pulsed primary magnetic fields on an organism, and furthermore this device does not include a significant feature of the present invention, namely the storage medium with its particular control device.

BRIEF DESCRIPTION OF THE DRAWINGS

The present invention is described in more detail below. In the explanatory drawing.

DESCRIPTION OF PREFFERED EMBODIMENTS

Figure 1:
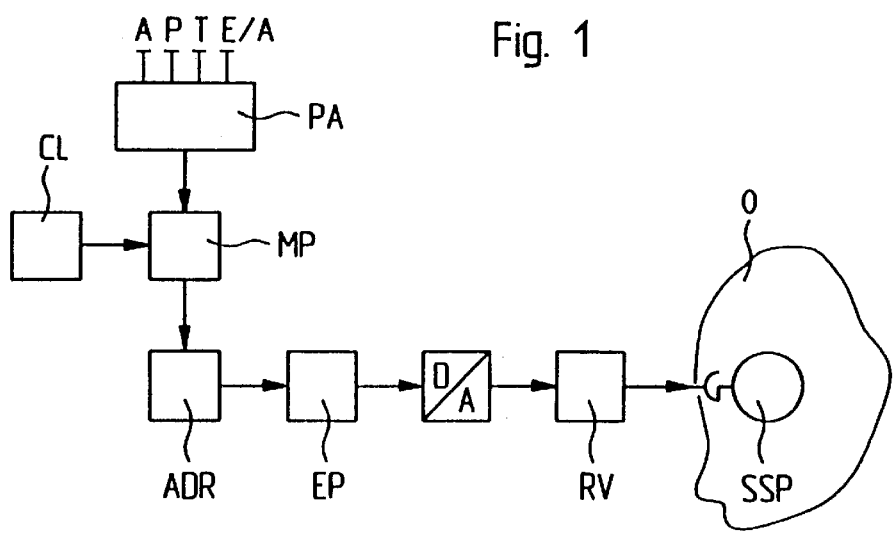
FIG. 1 shows a block circuit diagram of a device for generating pulsating magnetic fields on an organism.

The block circuit diagram in FIG. 1 corresponds to the block circuit diagram represented and described in German published document 42 21 739 A1 mentioned in the introduction. The following components are shown: PA—operating panel, MP—microprocessor, ADR—address memory and address generator, EP—memory, CL—pulse signal generator, A—adjuster for low pass amplifier, P—adjuster for reading sequence of the memory, T—adjuster for pulse timing, E/A—on/off switch, RV—low pass amplifier. In accordance with this, a transmitter coil SSP is supplied with appropriate currents. The transmitter coil generates a similar (primary) magnetic field in the organism O, whereby this magnetic field is phase-shifted in relation to the current in the transmitter coil. This primary magnetic field generates a (secondary) voltage in the organism O, whereby this voltage in turn induces a corresponding (secondary) current flow in the organism, such that the time sequence of this current flow is the first derivative of the primary magnetic field sequence. A (secondary) magnetic field is produced as a result of the (secondary) current, whereby the time sequence of this magnetic field corresponds to the secondary current flow sequence. The secondary magnetic field induces a current in a measurement coil MSP (FIG. 3) such that this current is the first derivative of the time sequence of the secondary current and is therefore the second derivative of the primary current which flowed in the transmitter coil.

FIG. 2 shows an impulse schedule illustrating the time sequence of the current in the transmitter coil SSP which affects the primary magnetic field. To aid better comprehension, the impulse schedule incorporates tried-and-tested values for the duration of the individual impulses and impulse intervals in milliseconds.

In the impulse schedule, a) reproduces the shape of the impulse referred to as the basic pulse, which has a repetition frequency of, for example, 200 Hz and an exponential top sequence. However, the basic pulse is not sent continuously. Rather, as shown in b), an impulse pause succeeds each package of four basic pulses. As shown in c), three such impulse packages, consisting of four basic pulses each and the corresponding impulse pauses, are sent in succession, followed by a further impulse pause. As shown in d), nine such packages of three are sent in succession, followed by a further impulse pause. Following this, the cycle is repeated for a duration of several minutes, for example two minutes.

Figure 3:
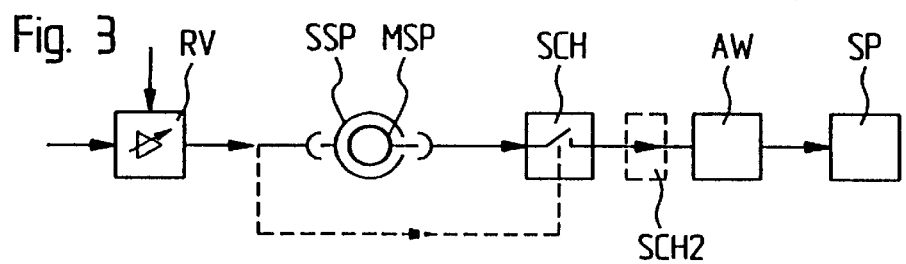
FIG. 3 shows a device in accordance with the present invention.
Figure 2A:
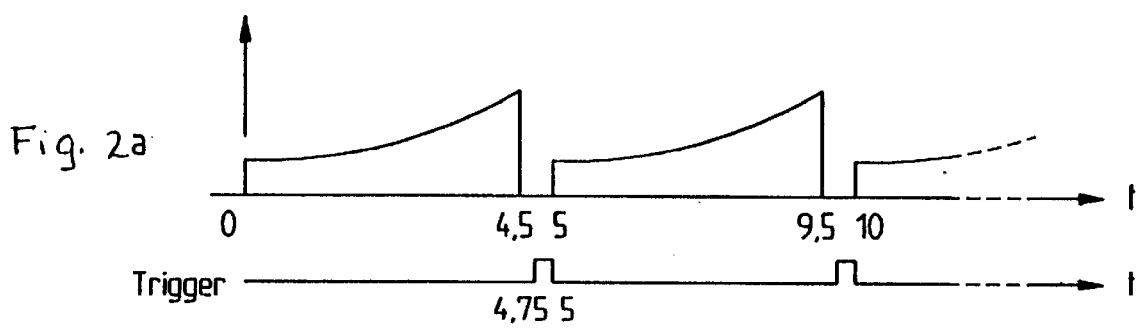
FIG. 2 shows an impulse schedule.
Figure 2B:
Figure 2C:
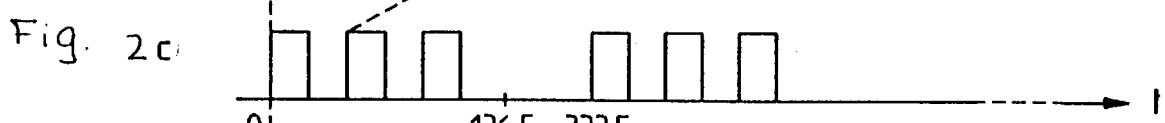
Figure 2D:
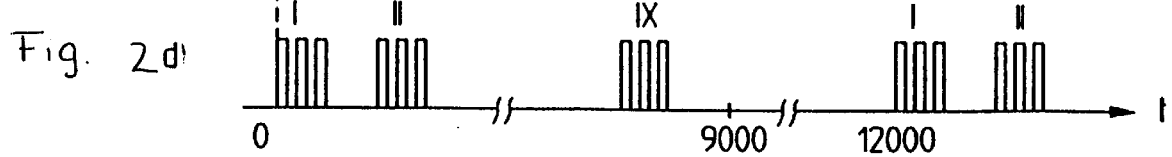

The secondary fields initiated in the organism O by the primary signal and its magnetic field are picked up by a device in accordance with the present invention, of which a block circuit diagram is presented in FIG. 3. Its basic design in this example corresponds to German published Document 42 21 739 A1 as mentioned in the introduction. However, a storage medium circuit SP is connected to the output of the suppression circuit SCH, which enables secondary field signals to be stored after they have been received by the measurement coil MSP following the individual basic pulses (see FIG. 2a). A current peak occurs in the measurement coil when the basic pulse is returned to the value zero and this current peak does not correspond to the required secondary field signal; for this reason, the connection to the storage medium SP is not established until this current peak has decayed. This can be achieved, as shown in FIG. 2 for example, by deriving a trigger impulse with a corresponding time delay from the basic pulse, whereby this trigger impulse serves to initiate the connection of the measurement coil to the evaluation circuit AW and the storage medium SP, and whereby this initiated connection lasts until the beginning of the next basic pulse. In this manner, a series of secondary field signals is received and stored in the storage medium SP for further evaluation.

Figure 4:
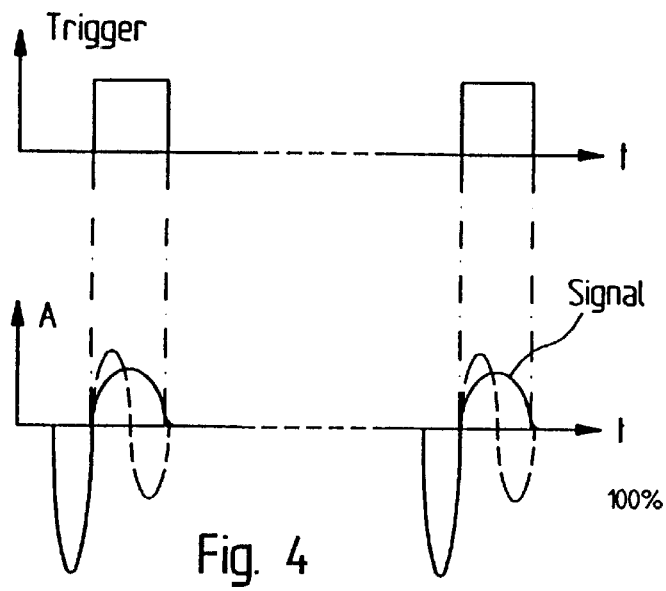
FIG. 4 shows the amplitude curve over time for a measured secondary field signal.

FIG. 4 shows the sequence of such a secondary field signal, in which time values are entered on the x-axis and amplitude values are entered on the x-axis. It can be seen that the secondary field signal is relatively weak and the corresponding disruptive signals such as noise and other disruptive fields can lead to not inconsiderable measurement errors. This is the same effect as an inadequate signal-to-noise ratio. The shape shown in FIG. 4 is the shape of a measured secondary field signal. In themselves, it is possible to derive the secondary field signals from any impulses of the primary impulse sequence. However, it has proven to be more effective if the derivation uses that sequence of basic pulses which produces a sequence frequency of, for example, 200 Hz given the relationships shown in FIG. 2.

The suppression circuit SCH is only engaged by the trigger impulse during the time when the secondary field signal of interest is present. By this means, it is not only the voltage peaks at the end of the individual impulse, shown as dashed lines in FIG. 4, which are suppressed, but also other undesirable signals which may occur during the duration of the suppression.

Figure 5:
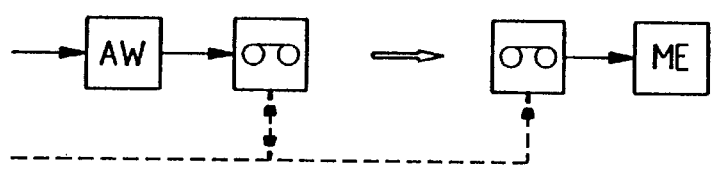
FIG. 5 shows an analogue device in accordance with the present invention, with a magnetic tape storage medium.

In a measurement taken over a specific period of time, secondary field signals occur in succession one after the other, generally as analogue signals. If for example, as shown in FIG. 5, a magnetic tape recording device is used as a storage medium, the individual signals are recorded on the magnetic tape in a successive geometrical sequence. Correspondingly, they can be used for further processing in a simple manner. Above all, it is possible to combine a sequence of individual recordings into a cumulative signal using a correlation process, in order to obtain a signal-to-noise ratio which is much improved in comparison to an individually recorded signal. In itself, correlation technology is a generally familiar procedure in telecommunications transmission engineering, and is, for example, dealt with in detail and with bibliographical references in the book "Korrelationstechnik" by Lange, 1960, VEB-Verlag, Berlin, in particular on pages 348 and 252 with regard to the details. The significant feature of the present application is that successive secondary field signals have almost identical amplitude sequences for a specific number of successive basic pulses and are therefore suited to algebraic addition, for example by reading out the successive secondary field signals one after the other and writing the readout results over each other in a phase-synchronous procedure using a pure process of addition. Interference signals such as noise and intermittent interference are by nature therefore not phase-synchronous and to a large extent add up in a geometrical fashion. Remaining phase-synchronous interference signals can be removed from the cumulative signal using a selective process by "cutting" them out of the cumulative signal using a time-windowing technique. This results in a signal which is well suited to further processing. FIG. 5 includes a schematic depiction of such a summation in a shared storage medium. A further magnetic tape recorder MAZ2 is supplied from the output of the magnetic tape recorder MAZ1. The magnetic tape in MAZ2 is designed as a closed loop and the length of its loop and the tape speed is adjusted to MAZ1 so that successive secondary field signals from MAZ1 are always recorded onto the same tape section of MAZ2. In this process, it must be ensured that the tape in MAZ2 is not deleted between the individual recordings. In order to guarantee that the time and phase synchronicity remains exact, it is recommended that synchronisation should be provided, for example by means of the trigger signal used for activating the suppression circuit SCH (FIG. 3); this is illustrated using the dashed line in the figure.

The cumulative signal can be brought to the actual measurement device ME by the play-back head of MAZ2. The measurement device ME can be an oscilloscope, a measurement device for determining the maximum amplitude of the signal, or—see FIG. 4—an integrator for determining the area covered by the secondary field signal corresponding to its energy content.

The phase and time synchronicity between MAZ1 and MAZ2 can also be ensured by deriving the synchronisation for MAZ2 from the signal output of MAZ1. To this end, for example, MAZ1 can record the trigger signal or a synchronising signal in addition to the secondary field signal so that this trigger or synchronising signal can be evaluated in MAZ2 in order to provide synchronisation. Additionally, this method makes it possible to separate in time the actual signal recording by measurement coil MSP from the actual evaluation by MAZ2.

Figure 6:
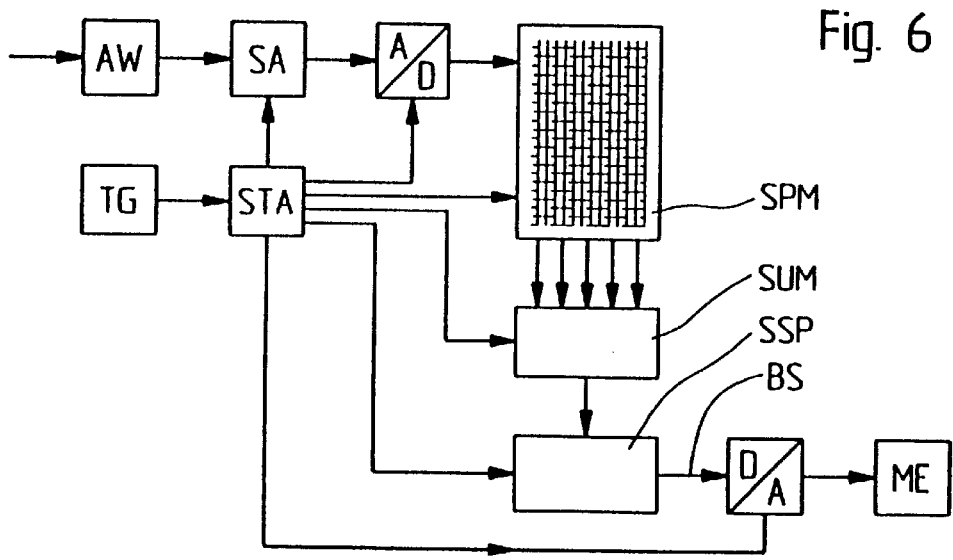
FIG. 6 shows a digital device in accordance with the present invention, with a matrix storage medium structure.

Instead of using an analogue storage method, a digital method can be used to beneficial effect. In this case, as shown in FIG. 6, the secondary field signals are sampled in a sampler SA having a correspondingly high sampling frequency. The individual samples are converted into a digital signal using a device referred to as an analogue-digital converter A/D. Thus, in a procedure of prior art, one obtains a series of digital signals, each of which represents the amplitude value of a sample, and which can be stored in a storage medium for further processing. In this case, It is to be recommended that the digital signals from successive secondary field signals should be written in successive lines to a memory SPM organised in the form of a matrix, so that the individual, digitally written secondary field signals are positioned one above the other in the matrix. All that is then required for the evaluation is to digitally total the values located one above the other in the columns of the matrix using an adder SUM and to store the totals in the correct column in a sum memory SSP. The corrected signal BS can then be taken from the sum memory SSP and be converted into an analogue signal using a digital-analogue converter of prior art and used as illustrated in FIG. 5. However, the corrected signal can also be evaluated correspondingly as a digital signal using a procedure of prior art.

The memory matrix can be read out in series in the same way as the results of the SUM are written to the sum memory SSP. Thus it is possible to use procedures of prior art to change from SPM, SUM and SSP without requiring many connections.

According to prior art, timing signals are required for the sequences of the individual circuit modules (SA, A/D, SPM, SSP, SUM, D/A), and these timing signals are supplied by a shared timing signal generator TG using a control signal derivation circuit STA in a procedure of prior art.

The addition of a storage medium to the evaluation circuit is a simple means of opening up a series of evaluation options providing different levels of qualitative and quantitative information. Both the amplitude of the current induced in the measurement coil following each impulse and the energy transmitted into the measurement coil by the organism following each impulse are significant parameters for determining the effect which the individual impulse is having on the organism subjected to the impulses with respect to ion transport. This is especially applicable to basic current pulses having a repetition frequency between 100 Hz and 1000 Hz, and preferably 200 Hz. The secondary field signals or feedback signals are the second derivative of the primary signals and their amplitude sequence is determined by the organism in question. The second derivative can be used to derive the following items of information, amongst others:

1. The second derivative is a measure of an increased volume of electrolyte (blood, lymph, extra-cellular fluid) due to an increased ion flow absorption (increased displacement current) in the electromotive field. The principal measure is the height of the first amplitude in a cycle of four impulses of a 200 imp./sec. series (see FIG. 2). Physiologically, this corresponds to increased central and peripheral blood flow in an organism (increased dilation of blood vessels and more profuse blood flow).

2. It is a measure of the polarisation amplitude of the boundary areas affected, due to:

a. The neutralisation and possible changeover in charge of the contact potential between the "fluid" and "solid" phases, in other words between the electrolyte and the vessel wall or membrane.

b. The size of the capacitive charge, whereby the amount of ions applied for boundary area polarisation is proportional both to the volume of electrolyte (see 1.) and to the induced electromotive force, in other words it is also proportional to the size of the induced area.

The measure for this is the shape change in the feedback impulse peaks and the falling height of the second, third and fourth impulse amplitudes within the four-impulse cycle of the 200 imp./sec. series. Physiologically, this corresponds to the pH change caused by rapid proton migration in the electromotive force field and liberation of $Ca^{++}$ from proteins in case of a pH reduction, and $Ca^{++}$ bonding in case of a pH increase.

In turn, the effects described in 1. and 2. correlate to:

Increased partial oxygen pressure ($pO_2$) in the tissue cells

Increased substrate supply to the tissue cells

Increased disposal of metabolic products by the tissue cells

Forced acceleration of activity in the immune system, in particular concerning the activity of macrophages Increased activity by certain enzymes Increased cell regeneration, and Increased flow of information These correlated parameters are evaluated by measuring the contents of the area in the secondary field sequence, i.e. the feedback impulse voltage—time curve, which is the cumulative feedback impulse area for several cascades of impulses each consisting of four impulse cycles each. This area can be displayed continuously as a general evaluation of the current degree of blood circulation. A change, in particular an increase, in the specific cumulative area value of each impulse cascade can be compared to the area value of the previous impulse cascade to provide decisive information about the effect of the physical therapy system or the changes initiated by drugs (promotion of blood flow), sport and other such influences. It is therefore to be recommended that these changes should be shown on a separate display device. For each unit of time, the area value adopts a greater value in particular when there is Increased blood circulation and/or lymph circulation compared to the initial condition (in the case of lymph circulation, when the polarisation of the boundary areas is not excessive). By such means, it is possible to evaluate applied amplitudes and the duration of the magnetic field of the medicament, movement, etc.; in other words, to evaluate the dose precisely in view of its effect on the organism.

Under certain circumstances, the measurement of breathing organisms is modulated considerably by the movements involved in breathing, since the distance between the measurement coil and the organism changes unless appropriate measures are taken to prevent this. This can produce disruptive effects, particularly during more lengthy measurement cycles. One method of alleviating this problem is to use means of attaching the measurement coil firmly onto the organism. Another possibility is based on the fact that the breathing frequency is considerably different from the repetition frequency of the secondary field signals. It is therefore possible, for example by means of infrared photoelectric barriers, to determine specific time phases for breathing during which the distance between the measurement coil MSP and the organism O is within specific tolerances, and only to send the secondary field signals picked up by MSP during these time phases onwards to evaluation, for example by means of allocating a further suppression switch SCH2 to SCH—shown by a dashed line in FIG. 3—which only activates the circuit during these periods.

Figure 7:
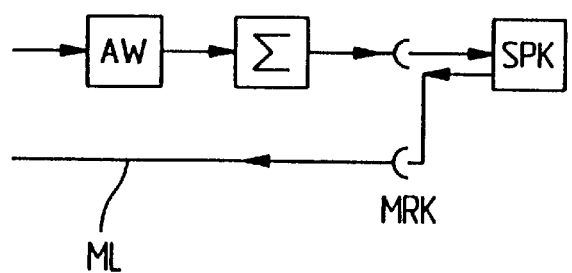
FIG. 7 shows a device in accordance with the present invention with an external memory medium card.

A configuration in accordance with the present invention also opens up the possibility of determining and recording the long-term effect of magnetic field treatment. This purpose can be served by a storage medium which is external of the device, such as a patient's card. This patient's card can be a card with a memory chip as is familiar from prior art, for example as described in the book "Chipkarten—Technik, Sicherheit, Anwendungen" by Fietta, Verlag Dr. Alfred Huttig, 1989, Heidelberg (in particular the reference on page 132 regarding such purposes). It is beneficial if the device for storing data in the external storage medium, such as a patient's card, SPK has a blocking device which only permits the device to be taken into operation when the external storage medium is located in the appropriate accommodation point for it in the device, and is capable of being written to. In FIG. 7, this is indicated by means of a response contact MRK or a switch which passes authorisation for the device to be used through a response line ML. Such blocking devices are familiar from prior art, for example as used in personal computer floppy disc drives, so that there is no need to enter into further detail on this point.

Figure 8:
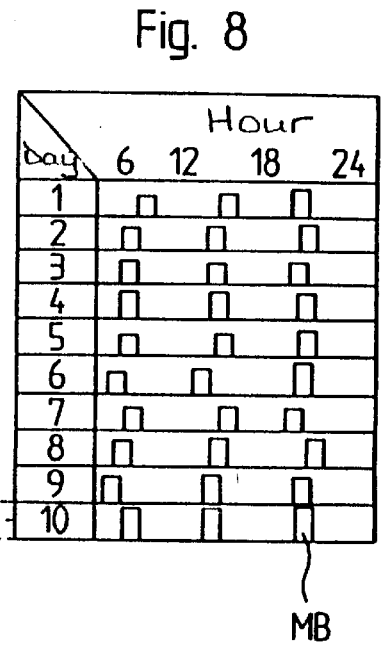
FIG. 8 shows an advantageous configuration of an external memory card for storing the changes arising during the treatment of an organism.

As shown in the example in FIG. 8, such a patient's card is used for storing the sum of all the differences in the impulse cycles, for example all increases, for the period of therapy or of measurement of, for example, seven minutes per session of treatment. This recording can, for example, use a number between 1 and 100 which represents the percentage growth in relation to the first cycle (=the initial measurement in absolute terms or relative to a particular day), whereby growth of 100% indicates a doubling of the feedback amplitude and corresponds to approximately double the volume of blood or lymph at the end of the treatment compared with the first measurement. This can also be evaluated for conversion into a depiction of the success achieved during the day.

If, as assumed in FIG. 8, the card is configured as a visually legible card, it is to be recommended that the data structure on the card be designed so that the data from one day of treatment are stored in one line each, and that these lines are written one under the other. The form of depiction shown in the figure is for three measurements per day or 24-hour period and ten successive days of treatment. The differences between the starting value in each case and the corresponding finishing values are entered on the card as measurement bars MB.

For the measurement, it has proven to be advantageous if approximately one hundred successive secondary field signals are combined into one measurement value. This corresponds to a measurement duration of approximately 500 milliseconds. If this measurement is taken both as the beginning and the end of the treatment of an organism lasting, for example, for seven minutes, it is possible to form the differential value between both measurement values, which is determined by the change due to the specific treatment of the organism. The evaluation of the correlation of each package of one hundred secondary field signals produces a considerable improvement in the signal-to-noise ratio.

The use of a storage medium makes possible a further method of evaluating the secondary field signal. If a differentiating element is connected to the memory SP (FIG. 3), it provides a signal at its output which enables conclusions to be drawn using the fine structure of the secondary field signal, whereby these conclusions have been familiar for many years in a similar form for evaluating electrocardiograms. Therefore, this makes it easier to recognise the mechanisms of the effect as well as the effects of ions to be transported within an organism by the magnetic fields. The differentiating element is, in a preferred embodiment, connected after the memory SP and before the actual measurement device. Its output signal can also be stored in a storage medium for further processing. FIG. 4 shows as a dotted line the sequence of a signal which can be obtained using differentiation. It is also possible to connect the differentiating element before the memory and store the result of the differentiation in the memory for further processing.

As shown by investigations upon which the present invention is based, the time when an organism is subjected to magnetic fields is of considerable importance. The sleep hormone melatonin can be suppressed by magnetic fields, so treatment should not take place if the organism needs sleep, whereas treatment is appropriate if the organism needs to stay awake. Furthermore, the level of adrenaline influences the effect, so it is to be recommended that the time of treatment be selected as late in the morning (11:00 +/–2 hours) and/or late in the afternoon (16:00 +/–2 hours), since the level of adrenaline is at its highest at these times during the circadian rhythm of human beings.

Figure 9:
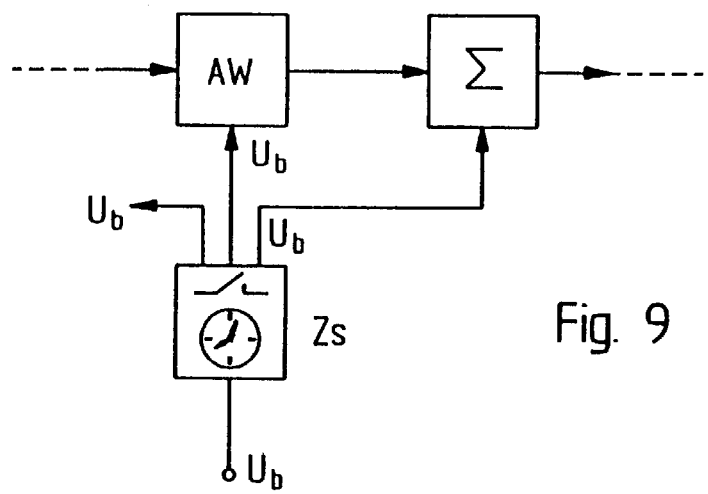
FIG. 9 shows a block circuit diagram for a device in accordance with the present invention with a timer blocking device.

This can be achieved, as shown schematically in FIG. 9, by providing a timer switch ZS which operates, for example, by interrupting the operating voltage $U_b$ to the evaluation circuit AW and/or further parts of the device such as the sum memory, however in particular to the generator for supplying the magnetic field coil at times outside those mentioned above, and therefore preventing the device from being operated.

As shown in particular by further investigations upon which the present invention is based, exposing an organism to a magnetic field leads to increased oxygen diffusion due to the increase in partial oxygen pressure in the tissue. In fact, it causes the blood vessels to dilate. Equally, the temperature of the organism rises. The individual signals can be derived using chemical sensors in addition to a measurement pick-up responding to the secondary magnetic field, whereby the chemical sensors particularly take the form of gas sensors and/or sensors which respond to heat radiation. These different sensors can be used individually and in combination with one another.

A configuration involving individual signal derivation from respiratory air using gas sensors to detect the gases nitrogen monoxide, hydrogen chloride and carbon monoxide has proven to be particularly effective. Such sensors and their circuit engineering are familiar from prior art, for example in the book mentioned above, "Mikroelektronische Sensoren" pages 111 to 137.

Figure 10:
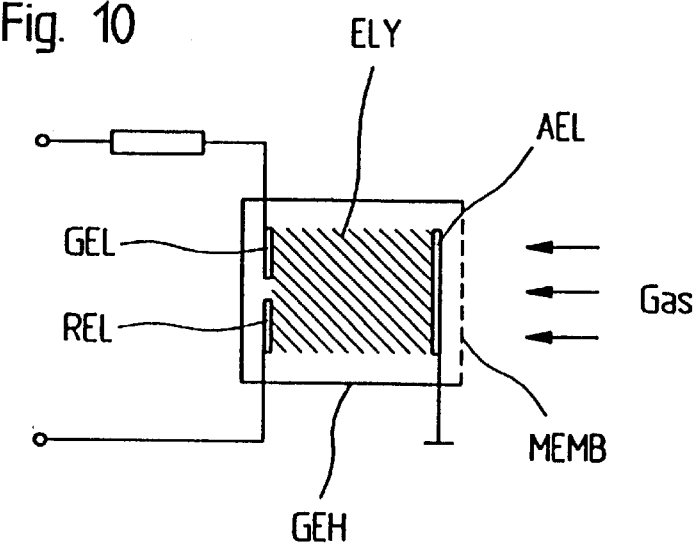
FIG. 10 shows a section through a gas sensor of prior art which can be used in a device in accordance with the present invention, and FIG. 11 a breathing mask with a gas sensor.

FIG. 10 presents a schematic section through a gas sensor as formed, for example, in device G 818 of the "Gesellschaft für Gerätebau" in Dortmund. An operating electrode AEL, reference electrode REL and a counter electrode GEL are located in a housing GEH which has a gas-permeable membrane MEMB. The space between the electrodes is filled with a suitable electrolyte ELY which reacts with the gas introduced into the sensor through the membrane and thereby causes the electrical values existing between the electrodes to change. Device G 818 is used for measuring nitrogen monoxide emissions from combustion engines, amongst other applications. This sensor is a semiconductor sensor in which the current flowing through it is used as the measurement parameter. The current produces a potential in the resistor through which it flows, which is proportional to the gas concentration and is used as the signal.

Figure 11:
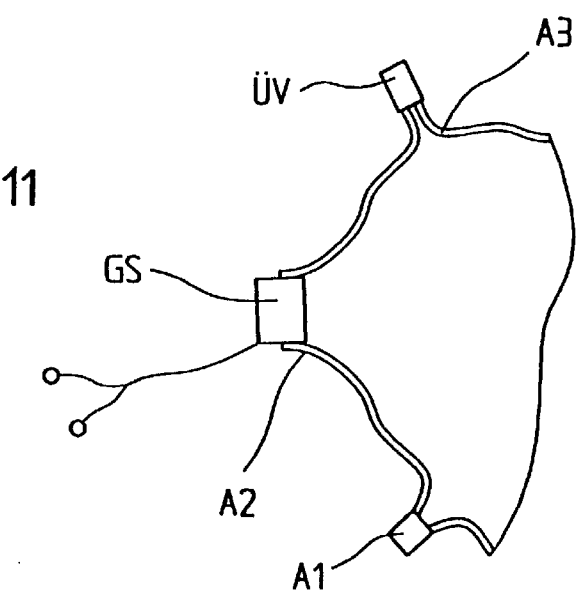

It is advantageous if the gas sensor is integrated into a breathing mask which takes the form of a tried-and-tested model enclosing the nose and chin area of a human being, as shown in FIG. 11, and has three connections. A first connection A1 serves to connect the mask to a pressure pump which is not illustrated and which delivers ambient air into the breathing mask. A second connection A2 contains the gas sensor GS and an electrical line runs from this connection to a device which is not illustrated, whereby the electrical line conducts the electrical parameters registered by the gas sensors. A third connection A3 contains a pressure relief valve ÜV which guarantees that the pressure in the breathing mask remains constant, so the gas sensor is operating under clearly reproducible measurement conditions. The pressure pump, which is not illustrated, should produce a pressure which is rather low and merely high enough to ensure that the respiratory air can reliably escape in the region of the gas sensor GS. An excess pressure of 20 to 80 millibars in relation to the outside air pressure has proven to be beneficial.

Instead of the breathing mask illustrated with its pressure pump connection, it is also possible to use a mask without a pressure pump, whereby such a mask is of the gas mask type with an intake and outlet valve for the respiratory air. The gas sensor is to be located in the exhalation air passage, similarly to the configuration shown in FIG. 11. However, this type of breathing mask demands that the organism exert a certain amount of additional energy during breathing.

The change in the respiratory air induced by the effect of a magnetic field is a somewhat delayed reaction to the actual time of the application of the magnetic field (a delay of some minutes), because not only the organism but also the gas sensor requires a certain amount of time to respond. However, the reaction is clearly apparent, particularly if the time windowing technique explained in FIG. 3 is used to select only useful values for the measurement and these are fed to the storage medium as individual signals for summation. By visualising the output signal on an oscilloscope display, it is possible to detect a signal which clearly indicates a change in the gas concentration, and whose duration corresponds relatively well to the duration of the preceding treatment period.

Instead of evaluating changes in the gases evolved by an organism, it is also possible to evaluate changes in its bodily fluids, in particular changes in the enzymes contained therein. The book mentioned above, "Mikroelektronische Sensoren" also describes and explains such sensors, so that in view of this, there is no requirement for a detailed description of these.

The device in accordance with the present invention is particularly important because it enables exposure to magnetic fields to be monitored and checked. Exposure of excessive duration can overwhelm the capacity of an organism to control the changes induced (for example an excess of $Ca^{++}$ in cells). In this case, it can be expected that pathological effects will follow. However, the diffusion of nitrogen monoxide in the lungs of an organism can serve as an indication of unphysiological moments.

The present invention is, of course, in no way restricted to the specific disclosure of the specification and drawings, but also encompasses any modifications within the scope of the appended claims.

What we claim is:

1. A device for determining the effect of pulsed primary magnetic fields on an organism, said device comprising:
   a measuring pick-up for secondary magnetic field signals generated by the organism in response to the primary magnetic fields;
   an evaluation circuit for said secondary magnetic field signals;
   said evaluation circuit comprising a first memory device with a memory unit;
   said evaluation circuit further comprising a control device;
   said control device comprising a means for processing sequentially received secondary magnetic field signals, wherein said sequentially received secondary magnetic field signals are written into said memory unit such that a cumulative magnetic field signal is generated in said memory unit; and
   wherein said cumulative magnetic field signal is used as an output signal of said evaluation circuit.

2. A device according to claim 1, wherein said measuring pick-up is a measuring coil.

3. A device according to claim 2, wherein, for ensuring comparability of said sequential secondary magnetic field signals, said measuring coil comprises means for securely attaching said measuring coil to the organism.

4. A device according to claim 2, further comprising an auxiliary coil for ensuring comparability of said sequential secondary magnetic field signals, wherein said second measuring coil is positioned remote from said measuring coil such that said auxiliary coil is exposed only to disruptive fields that also penetrate said measuring coil and wherein said measuring coil and said auxiliary coil are connected to an input of said evaluation circuit such that output signals of said measuring coil and said auxiliary coil are sent via an electric differential circuit to said input.

5. A device according to claim 1, wherein said evaluation circuit has a suppression circuit connected between said measuring pick-up and said memory unit, said suppression circuit comprising a control unit for allowing processing of said sequential secondary magnetic field signals only in a periods of rest after said primary magnetic pulses.

6. A device according to claim 1, wherein said control device is designed such that said cumulative signal is a mean value of said sequential secondary magnetic field signals.

7. A device according to claim 6, wherein said control device comprises a correlator for calculating said mean value, wherein said correlator performs an algebraic addition for said sequentially received secondary magnetic field signals and a geometric addition for disruptive signals.

8. A device according to claim 1, wherein said evaluation circuit, said memory unit and said control device are designed such that an amplitude of said sequential secondary magnetic field signals is determined.

9. A device according to claim 1, wherein said evaluation circuit, said memory unit and said control device are designed such that an energy contents of said sequential secondary magnetic field signals is determined.

10. A device according to claim 1, wherein said evaluation circuit, said memory unit and said control device are designed such that differential signals are calculated from said sequential secondary magnetic field signals and said differential signals are stored.

11. A device according to claim 1, comprising a second memory device for storing said cumulative signals.

12. A device according to claim 11, wherein said evaluation circuit and said control device are designed such that, at the beginning of subjecting the organism to the pulsed primary magnetic fields, said cumulative signals are sent to said second memory device.

13. A device according to claim 11, wherein said evaluation circuit and said control device are designed such that, at the end of subjecting the organism to the pulsed primary magnetic fields, said cumulative signals are sent to said second memory device.

14. A device according to claim 11, wherein said evaluation circuit and said control device are designed such that, at the beginning and the end of subjecting the organism with the pulsed primary magnetic fields, said cumulative signals are sent to said second memory device.

15. A device according to claim 11, wherein said second memory device is detachable from said device.

16. A device according to claim 15, wherein said second memory device is a chip card.

17. A device according to claim 16, wherein said second memory device comprises a plurality of sectors, wherein a first one of said sectors stores said cumulative signals as measured values, a second sector stores treatment parameters, and a third sector stores personal data of the organism.

18. A device according to claim 11, further comprising a device for applying the pulsed magnetic fields to the organism.

19. A device according to claim 18, further comprising a blocking device for allowing activation of said device only when said second memory device is operational.

20. A device according to claim 18, further comprising a blocking device for allowing activation of said device only during late morning hours and late afternoon hours.

21. A device according to claim 1, further comprising a circuit for deriving a trigger signal from movements of the organism in order to ensure comparability of said sequential secondary magnetic field signals, wherein said evaluation circuit has a trigger element and wherein said trigger signal is sent to said trigger element so that said evaluation circuit is operational only at specific times determined by said trigger signal.

22. A device according to claim 1, wherein said measuring coil comprises a means for shielding against exterior magnetic disruptive fields in order to increase the signal-to-noise ratio of said evaluation circuit.

23. A device according to claim 1, further comprising an auxiliary chemical gas measuring device for detecting gases emanating from the organism.

24. A device according to claim 23, further comprising a breathing mask, wherein said gas measuring device is integrated into said breathing mask.

25. A device according to claim 24, wherein said breathing mask comprises three connectors, wherein a first one of said connectors supplies compressed breathing air, a second one of said connectors receives said gas measuring device, and a third one of said connectors receives a controller for ensuring a substantially constant pressure for gas flow form a gas inlet of said measuring device to the exterior of said breathing mask.

26. A device according to claim 23, wherein said gas measuring device is a sensor for detecting at least one gas selected from the group consisting of HCl and NO.

27. A device according to claim 1, further comprising an auxiliary chemical measuring device for detecting organism-specific fluids.

28. A device according to claim 1, further comprising a radiation thermometer for detecting the temperature of the organism, wherein said thermometer has an output and provides the measured temperature value as an electric signal at said output.

29. A device according to claims 28, wherein said radiation thermometer is designed to measure the temperature of the organism in one of the bodily orifices of the organism.

30. A device according to claim 29, wherein said radiation thermometer measures the temperature of the organism in the ear of the organism.

* * * * *